United States Patent
Meinen

(10) Patent No.: US 9,903,802 B2
(45) Date of Patent: Feb. 27, 2018

(54) DRILLING FLUID MONITOR AND METHOD

(71) Applicant: Toby L. Meinen, Driftwood, TX (US)

(72) Inventor: Toby L. Meinen, Driftwood, TX (US)

(73) Assignee: Toby L. Meinen, Driftwood, TX (US)

( * ) Notice: Subject to any disclaimer, the term of this patent is extended or adjusted under 35 U.S.C. 154(b) by 414 days.

(21) Appl. No.: 14/627,097

(22) Filed: Feb. 20, 2015

(65) Prior Publication Data
US 2016/0245081 A1 Aug. 25, 2016

(51) Int. Cl.
*G01N 9/04* (2006.01)
*E21B 44/00* (2006.01)
*E21B 21/01* (2006.01)
*E21B 21/08* (2006.01)

(52) U.S. Cl.
CPC ............... *G01N 9/04* (2013.01); *E21B 21/01* (2013.01); *E21B 21/08* (2013.01); *E21B 44/00* (2013.01)

(58) Field of Classification Search
CPC G01N 9/04; E21B 44/00; E21B 21/01; E21B 21/08
USPC .... 73/152.19, 19.09, 433, 434, 866; 175/40, 175/42, 46, 48, 50, 206, 207; 177/50, 177/161, 162, 245, 253
See application file for complete search history.

(56) References Cited

U.S. PATENT DOCUMENTS

| | | |
|---|---|---|
| 7,556,106 B1 | 7/2009 | Meinen et al. |
| 2011/0241889 A1* | 10/2011 | Fromme ............... G01N 1/2226 340/632 |
| 2016/0030620 A1* | 2/2016 | Peterson ................ A61L 9/122 261/84 |

* cited by examiner

*Primary Examiner* — Robert R Raevis
(74) *Attorney, Agent, or Firm* — Kinney & Lange, P.A.

(57) ABSTRACT

A drilling fluid monitoring system includes a scale and a container disposed on the scale. A container inlet is disposed proximate a top of the container and a container outlet is disposed proximate a bottom of the container. A serpentine passage is disposed inside the container and is fluidically connected to the container inlet and the container outlet.

12 Claims, 5 Drawing Sheets

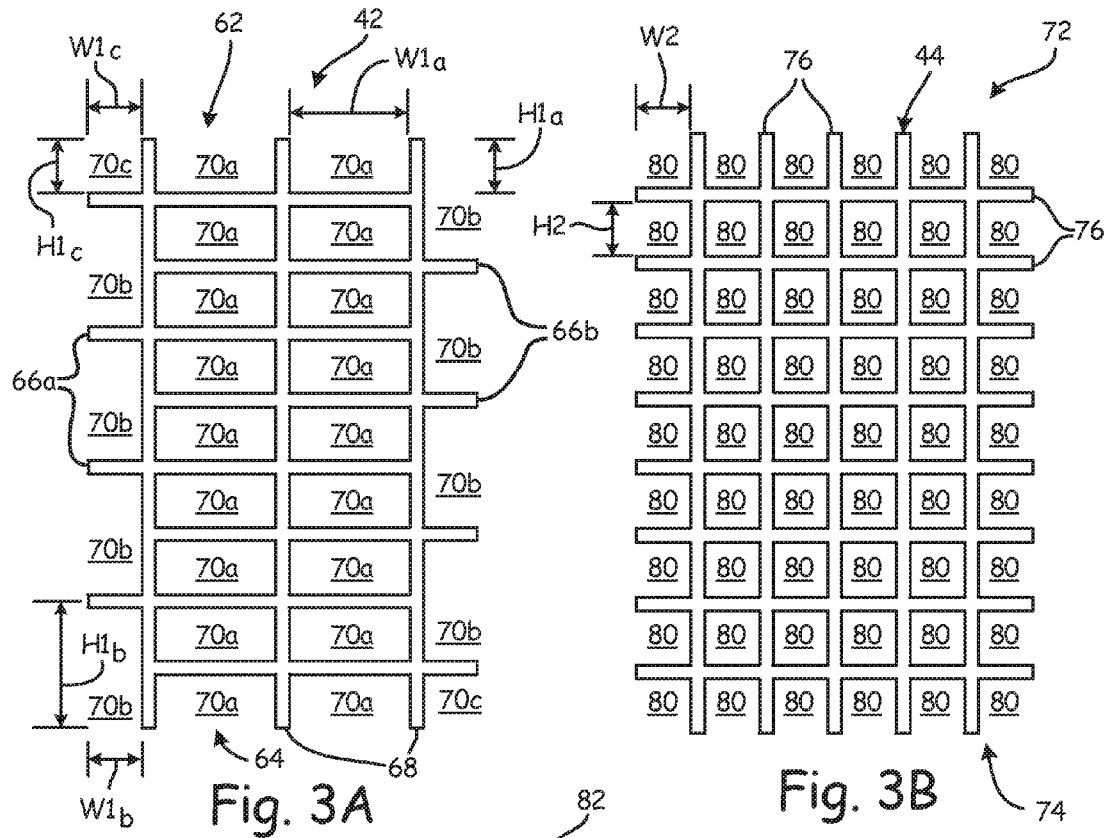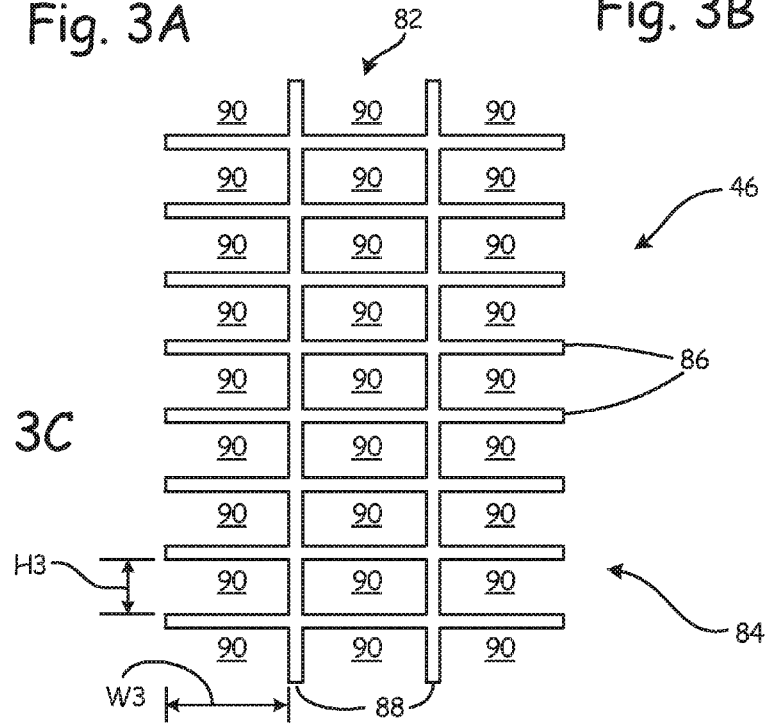

DRILLING FLUID MONITOR AND METHOD

BACKGROUND

The present disclosure relates generally to drilling fluid monitoring in subterranean drilling applications. More particularly, this disclosure relates to a method and system for monitoring the weight, mass, or density of drilling fluid.

During the drilling of a subterranean well in the quest for hydrocarbons, drilling fluid, also referred to in the art as "drilling mud," is circulated downwardly through a drill pipe and through a drill bit attached to the drill pipe. After exiting the drill bit, the drilling fluid flows into an annulus formed by the drill pipe and a bore wall of the well and return upwardly through the annulus to the surface. When the drilling fluid reaches the surface, the drilling fluid is directed to a shaker which separates cuttings from the drilling fluid. After passing through the shaker, the drilling fluid flows to a settling tank which is designed to further remove cutting particulates from the drilling fluid. The drilling fluid then travels to a suction tank where mud pumps return the drilling fluid back to the drill pipe and the well.

The drilling fluid is essential to a well drilling operation as the drilling fluid serves to carry the cuttings away from the drill bit area and out of the well. The drilling fluid also acts as a stopper in the well to prevent blowouts by exerting hydrostatic pressure on the bottom of the well to balance or overcome the pressure of any upwardly acting hydrostatic pressure disposed inside the formation adjacent to the well, such as the pressure of gas, water, or oil which may be exposed in drilling. While the hydrostatic pressure of the drilling fluid must be great enough to balance or overcome the formation pressure in the well, the hydrostatic pressure of the drilling fluid must also not be so great as to cause circulation losses of the drilling fluid in the well. Circulation losses occur when the hydrostatic pressure of the drilling fluid exceeds the formation pressure inside the well thereby causing the drilling fluid to escape out of the well and into the formation.

The drilling fluid generally includes caking agents that allow the drilling fluid to also seal the bore wall of the well. As the drilling fluid circulates through the well, the caking agents accumulate onto the surface of the bore wall of the well to seal the well and help prevent the drilling fluid from flowing out of the well and into the porous material of the formation.

As conditions vary in the course of drilling, the weight of the drilling fluid can also be affected by the changing conditions. For instance, if the drill bit penetrates a formation containing gas, the gas can enter the well and mix with the drilling fluid thereby reducing the density of the drilling fluid. Reducing the density of the drilling fluid can cause the drilling fluid to flow out of the well at a faster rate than the drilling fluid is entering the well, resulting in a loss of hydrostatic pressure of the drilling fluid in the well. Such a condition must be detected immediately as remedial action may be necessary to increase the density of the drilling fluid entering the well to restore balance between the hydrostatic pressure of the drilling fluid in the well and the formation pressure adjacent the well. If remedial action is not taken, the lack of balance between the hydrostatic pressure of the drilling fluid in the well and the formation pressure adjacent the well can result in a blowout of the well.

SUMMARY

In one aspect of the invention, a drilling fluid monitoring system includes a scale and a container disposed on the scale. A container inlet is disposed proximate a top of the container and a container outlet is disposed proximate a bottom of the container. A serpentine passage is disposed inside the container and is fluidically connected to the container inlet and the container outlet.

In another aspect of the invention, a method for monitoring drilling fluid used during drilling of a subterranean well includes pumping the drilling fluid into the subterranean well. The drilling fluid is then directed out of the subterranean well and into an inlet of a settling tank. A portion of the drilling fluid disposed proximate the inlet of the settling tank is pumped into an inlet of a drilling fluid monitoring system disposed proximate a top of the drilling fluid monitoring system. The portion of the drilling fluid then flows through a serpentine passage of the drilling fluid monitoring system that is fluidically connected between the inlet and an outlet of the drilling fluid monitoring system. The outlet of the drilling fluid monitoring system is disposed proximate a bottom of the drilling fluid monitoring system. A weight or mass of the portion of the drilling fluid flowing in the serpentine passage is measured by a scale connected to the serpentine passage. The portion of the drilling fluid flows out of the serpentine passage and into the outlet of the drilling fluid monitoring system.

In another aspect of the invention, a method for monitoring a drilling fluid during drilling of a subterranean well includes pumping a portion of the drilling fluid into an inlet of a drilling fluid monitoring system. The inlet is disposed proximate a top of the drilling fluid monitoring system and the drilling fluid monitoring system comprises a serpentine passage fluidically connected to the inlet and disposed on a scale. The portion of the drilling fluid flows through the serpentine passage of the drilling fluid monitoring system. The portion of the drilling fluid is then directed out of the serpentine passage through an outlet of the drilling fluid monitoring system disposed proximate a bottom of the drilling fluid monitoring system. A weight or mass of the serpentine passage and the portion of the drilling fluid disposed inside the serpentine passage is measured as the portion of the drilling fluid flows through the serpentine passage.

Persons of ordinary skill in the art will recognize that other aspects and embodiments of the present invention are possible in view of the entirety of the present disclosure, including the accompanying figures.

BRIEF DESCRIPTION OF THE DRAWINGS

FIG. 3A is a front elevation view of a panel used in the drilling fluid monitoring system from FIGS. 2A-2B.

FIG. 3B is a front elevation view of another panel used in the drilling fluid monitoring system from FIGS. 2A-2B.

FIG. 3C is a front elevation view of a third embodiment of a panel used in the drilling fluid monitoring system from FIGS. 2A-2B.

Figure 1:
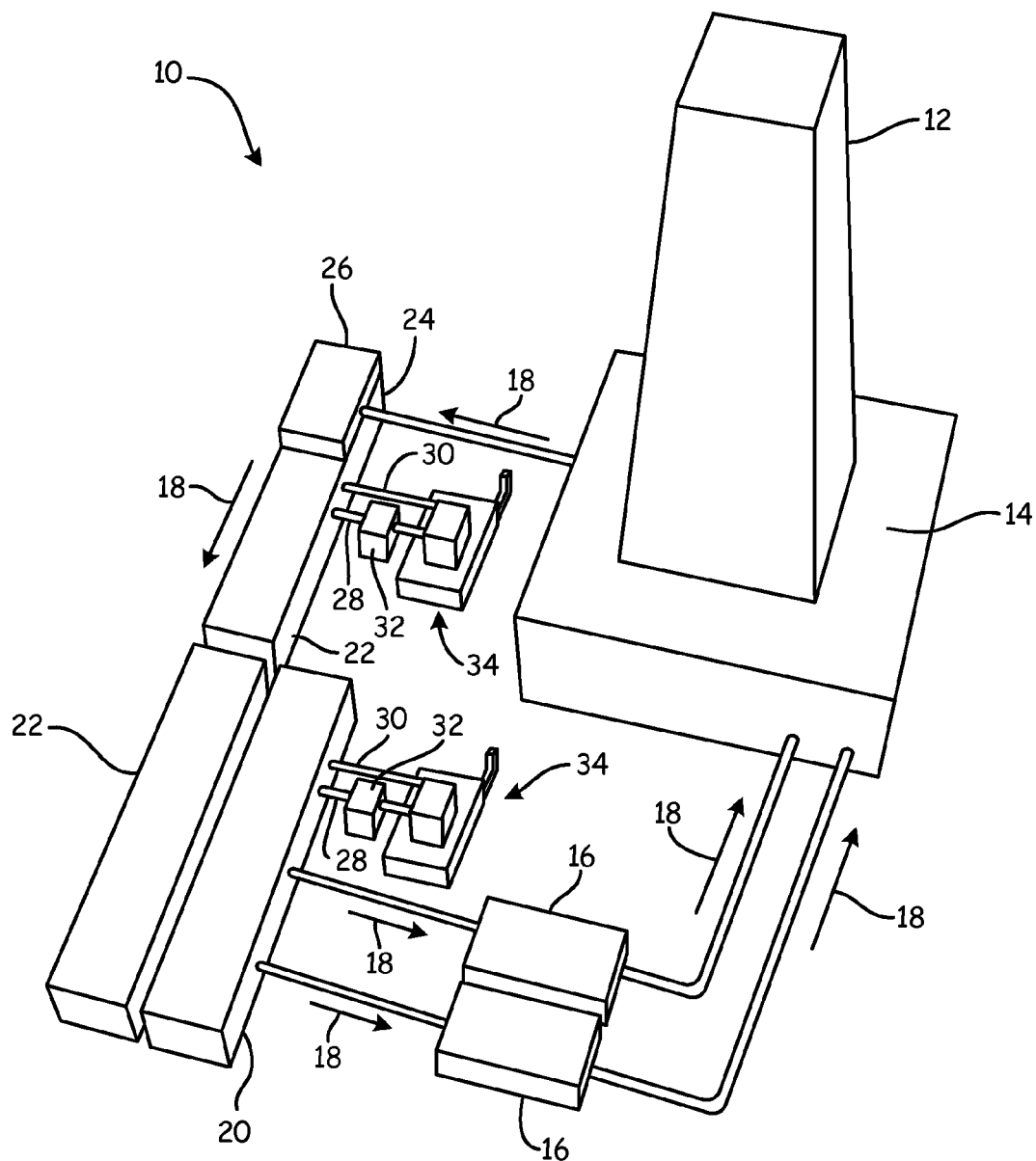
FIG. 1 is a schematic diagram of a drilling station.

While the above-identified drawing figures set forth one or more embodiments of the invention, other embodiments are also contemplated. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings. Like reference numerals identify similar structural elements.

DETAILED DESCRIPTION

The present disclosure provides a drilling fluid monitoring system to measure the weight of drilling fluid after the drilling fluid exits a subterranean well. The drilling fluid monitoring system includes a serpentine passage disposed on a scale. After the drilling fluid exits a subterranean well, a portion of the drilling fluid is routed to the serpentine passage of the drilling fluid monitoring system. As the drilling fluid flows without stopping through the serpentine passage, the scale measures the weight, mass, and/or density of the serpentine passage and the drilling fluid flowing inside the serpentine passage. Based on the weight, mass, and/or density of the drilling fluid measured by the scale, the weight or density of the drilling fluid can be adjusted before the drilling fluid returns to the subterranean well. A non-limiting embodiment of the drilling fluid monitoring system is shown in FIGS. 1-4, which are discussed below in detail.

FIG. 1 is a schematic diagram of drilling station 10. As shown in the schematic diagram of FIG. 1, drilling station 10 can include derrick 12, subterranean well 14 disposed beneath derrick 12, mud pumps 16, drilling fluid 18, suction tank 20, settling tanks 22, settling tank inlet 24, and shakers 26. Drilling station 10 can further include diversion lines 28, return lines 30, auxiliary pumps 32, and at least one drilling fluid monitoring system 34.

Derrick 12 is positioned above subterranean well 14 and can support a drilling assembly (not shown) for creating and expanding well 14. During drilling of well 14, mud pumps 16 pull drilling fluid 18 from suction tank 20 and push drilling fluid 18 into well 14. Drilling fluid 18 then travels through the drilling assembly to a bottom of well 14 where drilling fluid 18 exits the drilling assembly. After exiting the drilling assembly, drilling fluid 18 travels back to the surface in the annular space formed between the drilling assembly and the walls of well 14. As drilling fluid 18 travels back to the surface, drilling fluid 18 can clean well 14 by carrying cuttings out of well 14. After drilling fluid 18 returns to the surface, drilling fluid 18 exits well 14 and enters shakers 26. Shakers 26 are positioned proximate settling tank inlet 24 and help remove the cuttings carried by drilling fluid 18 before drilling fluid enters settling tanks 22. The cuttings not removed from drilling fluid 18 by shakers 26 settle out of drilling fluid 18 inside settling tanks 22 before drilling fluid 18 enters suction tank 20 and returns to well 14.

In addition to carrying and removing cuttings out of well 14, drilling fluid 18 can also carry gases or other fluids out of well 14 that enter well 14 from the formations surrounding well 14. These gases or other fluids can become entrained in drilling fluid 18 thereby lowering the density of drilling fluid 18, causing drilling fluid 18 to flow out of well 14 at a faster-than-intended rate. If the density of drilling fluid 18 is left unchecked, a loss of hydrostatic pressure of drilling fluid 18 in well 14 could occur, thereby possibly causing a blowout event in well 14. Drilling fluid monitoring system 34 can continuously or periodically measure the weight, mass, or density of drilling fluid 18 to help avoid a loss of hydrostatic pressure of drilling fluid 18 in well 14. Conversely, drilling fluid monitoring system 34 can also continuously or periodically measure the weight, mass, or density of drilling fluid 18 to help avoid an undesirable increase in weight of drilling fluid 18.

Figure 2A:
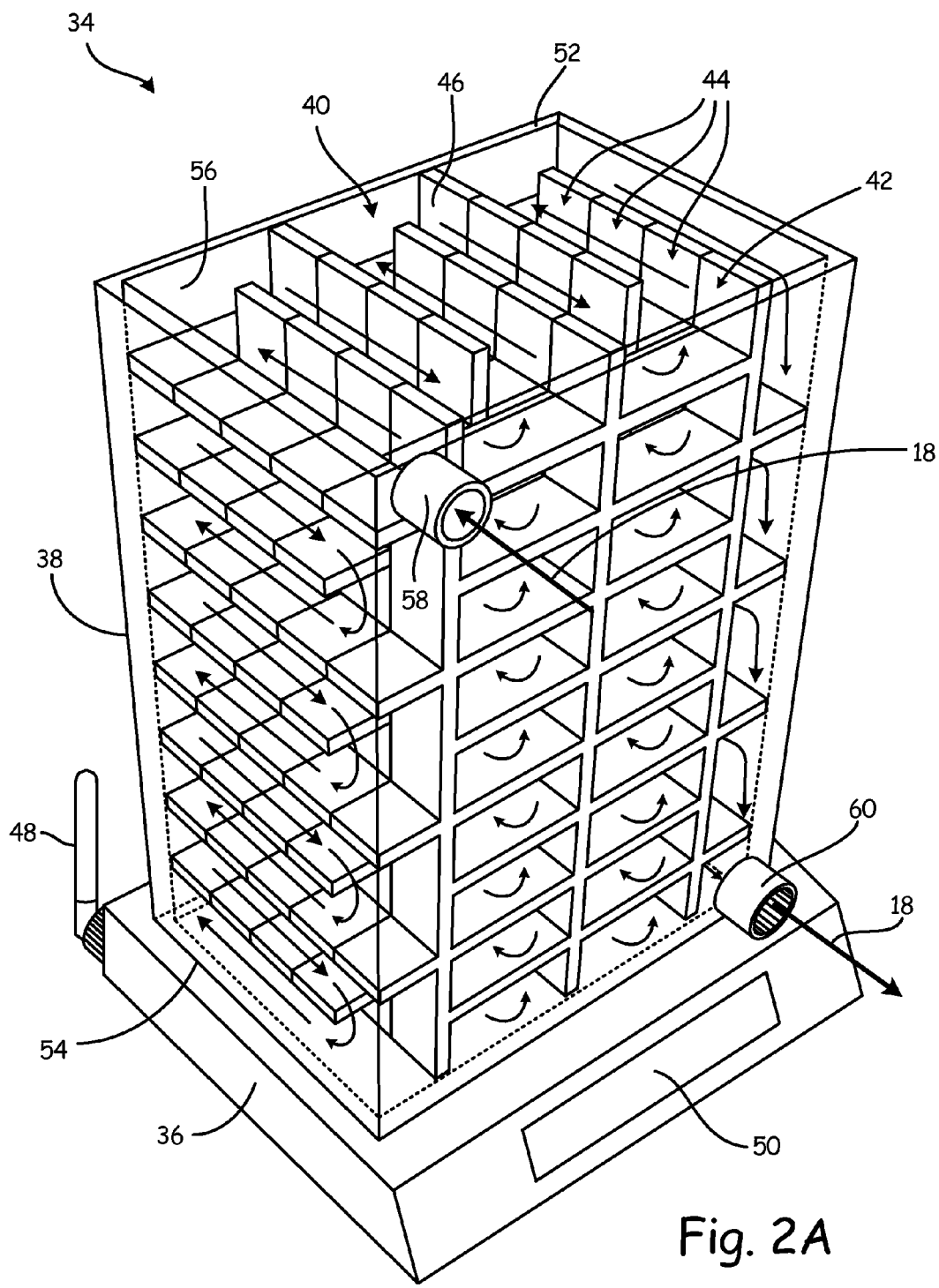
FIG. 2A is a perspective view of the drilling fluid monitoring system from FIG. 1.
Figure 2B:
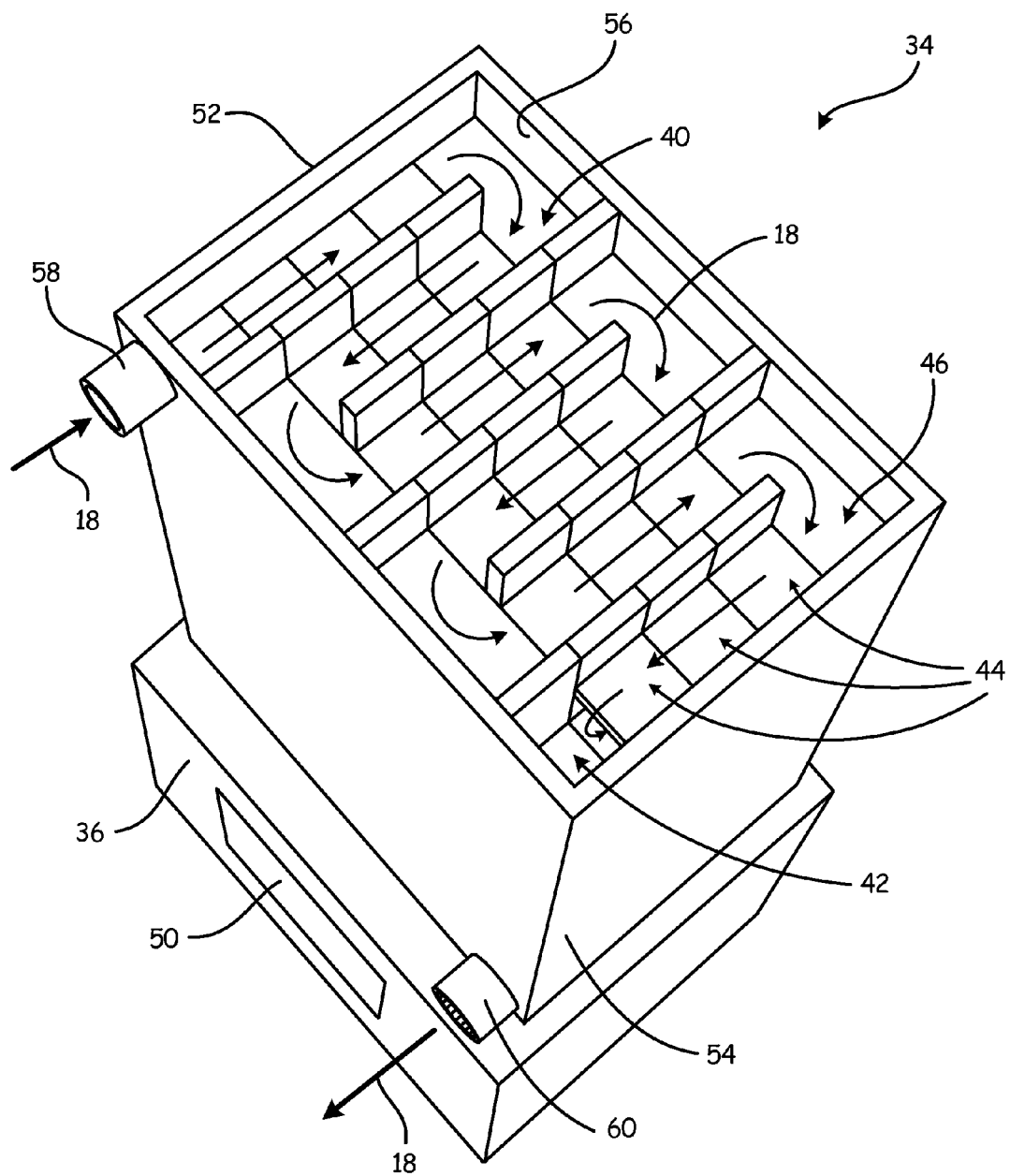
FIG. 2B is another perspective view of the drilling fluid monitoring system from FIG. 2A.

Diversion line 28 and return line 30 can fluidically connect drilling fluid monitoring system 34 to one of settling tanks 22 proximate settling tank inlet 24. Auxiliary pump 32 is connected to diversion line 28 and pumps a portion of drilling fluid 18 disposed inside settling tank 22 proximate settling tank inlet 24 into drilling fluid monitoring system 34. In the embodiment of FIG. 1, drilling fluid monitoring system 34 is enlarged and not drawn to scale. After entering drilling fluid monitoring system 34, drilling fluid 18 flows through drilling fluid monitoring system 34 without stopping and returns to settling tanks 22 via return line 30. As drilling fluid 18 flows through drilling fluid monitoring system 34, drilling fluid monitoring system 34 measures a weight of drilling fluid 18. After drilling fluid monitoring system 34 measures the weight of drilling fluid 18, the weight measurement of drilling fluid 18 can be compared to a baseline weight of drilling fluid 18 to determine whether the weight or density of drilling fluid 18 has changed during drilling. If the weight or density of drilling fluid 18 has changed, the weight or density of drilling fluid 18 can be adjusted to maintain the hydrostatic pressure balance in well 14. Drilling station 10 can include more than one drilling fluid monitoring system 34. As shown in FIG. 1, drilling station 10 can include a second fluid monitoring system 34 fluidically connected to suction tank 20. The second fluid monitoring system 34 can be used as a verification mechanism to determine whether any adjustments made to drilling fluid 18 at the surface have correctly modified the weight of drilling fluid 18 needed to maintain the hydrostatic pressure balance in well 14 before drilling fluid 18 reenters well 14. FIGS. 2A-2B, discussed in greater detail below, show an embodiment of fluid monitoring system in greater detail.

FIGS. 2A-2B will be discussed concurrently. FIG. 2A is a perspective view of drilling fluid monitoring system 34 and FIG. 2B is another perspective view of drilling fluid monitoring system 34. As shown in FIGS. 2A-2B, drilling fluid monitoring system 34 can include scale 36, container 38, serpentine passage 40, front panel 42, middle panels 44, and back panel 46. Scale 36 can include wireless transmitter 48 and display 50. Container 38 can include top side 52, bottom side 54, interior 56, container inlet 58, and container outlet 60.

As shown in FIGS. 2A-2B, container 38 can be a four-sided box that encloses interior 56 with bottom side 54 disposed on scale 36. Container inlet 58 is disposed proximate top side 52 of container 38 and container outlet 60 is disposed proximate bottom side 54 of container 38. Container inlet 58 is connected to diversion line 28 (shown in FIG. 1), and container outlet 60 is connected to return line 30. While top side 52 of container 38 appears to be open in FIGS. 2A-2B for ease of illustration, top side 52 is closed to atmosphere during operation of fluid monitoring system 34.

Serpentine passage 40 is disposed inside container 38 and is fluidically connected to container inlet 58 and container outlet 60. Serpentine passage 40 can include multiple interconnected levels that descend from top side 52 towards bottom side 54 of container 38. As drilling fluid 18 enters serpentine passage 40 via container inlet 58, drilling fluid 18 travels across a top level of serpentine passage 40, as shown in FIG. 2B, before descending downward to the level just beneath the top level. Drilling fluid 18 continues to travel across each level of serpentine passage 40 in like manner without stopping until drilling fluid 18 exits serpentine passage 40 through container outlet 60. Upon exiting serpentine passage 40 through container outlet 60, drilling fluid 18 returns to settling tanks 22 or suction tank 20 via return line 30 (shown in FIG. 1). Because container inlet 58 is disposed proximate top side 52 of container 38, and container outlet 60 is disposed proximate bottom side 54 of container 38, drilling fluid 18 can drain out of serpentine passage 40 and container 38 without the need for flushing when drilling fluid monitoring system 34 is powered down or disconnected for servicing. It is beneficial that all of drilling fluid 18 drain out of drilling fluid monitoring system when not in operation so as to prevent caking agents in drilling fluid 18 from bonding to and building up within serpentine passage 40.

As drilling fluid 18 is flowing through serpentine passage 40, scale 36 measures the weight of container 38, serpentine passage 40, and drilling fluid 18 disposed inside serpentine passage 40. Because container 38 and serpentine passage 40 should not change in weight, and because container 38 and serpentine passage 40 created a fixed volume, scale 36 can determine and output the weight, mass, and/or a density of drilling fluid 18 flowing through serpentine passage 40. For the purposed of this description, the embodiment of scale 36 shown in FIGS. 2A and 2B is configured to measure and output the weight drilling fluid 18. The embodiment of serpentine passage 40 shown in FIGS. 2A and 2b can have a total flow volume of approximately 3.79 dm$^3$ (1.00 gal). During operation, scale 36 can output a weight measurement of drilling fluid 18 to display 50 and/or wireless transmitter 48. Display 50 can be a digital display that can visually output the weight measurement of drilling fluid 18 for an operator to read in-person at drilling station 10. Wireless transmitter 48 can periodically or continuously transmit the weight measurement to a receiver disposed onsite at drilling station 10, or to a receiver disposed remotely. By transmitting the weight measurement of drilling fluid 18 to a receiver disposed remotely, drilling monitoring system 34 allows for remote monitoring of drilling fluid 18 that can be used to help guard against human error at drilling station 10. Based on the weight measurement outputted by scale 36 of drilling fluid monitoring system 34, an operator or an automated mechanism can modify the weight or density of drilling fluid 18 by adding additives, such as barite, to drilling fluid 18, or by mixing or replacing drilling fluid 18 with a drilling fluid having a different weight or density than drilling fluid 18.

As discussed above, drilling fluid 18 flows continuously (defined as flowing without stopping) through serpentine passage 40. In addition to flowing continuously through serpentine passage 40, drilling fluid 18 can flow through serpentine passage 40 at a substantially constant flow velocity or flow rate. Drilling fluid 18 can flow through container inlet 58, serpentine passage 40, and container outlet 60 at a flow velocity of approximately 2.27 m$^3$/h (10 gpm) to approximately 4.54 m$^3$/h (20 gpm). Serpentine passage 40 can include a uniform cross-sectional flow area throughout a full length of serpentine passage 40 so as to help reduce changes in the velocity and flow rate of drilling fluid 18. The cross-sectional flow area throughout the length of serpentine passage 40 can be approximately 4.83 cm$^2$ (0.75 in$^2$) to approximately 7.29 cm$^2$ (1.13 in$^2$). Because drilling fluid 18 flows through serpentine passage 40 at a substantially constant flow rate, caking agents disposed within drilling fluid 18 do not separate out of drilling fluid 18 and bond to serpentine passage 40 as drilling fluid 18 travels through drilling fluid monitoring system 34. During a non-public experimental test, the embodiment of drilling fluid monitoring system 34 was allowed to operate continuously for a duration of 30 days. During that 30 day period, drilling fluid 18 flowed continuously through serpentine passage 40 without the caking agents in drilling fluid 18 bonding to and clogging serpentine passage 40. It is preferred that the flow velocity of drilling fluid 18 be maintained between the range of approximately 2.27 m$^3$/h (10 gpm) to approximately 4.54 m$^3$/h (20 gpm). Should the flow velocity of drilling fluid 18 fall below 2.27 m$^3$/h (10 gpm), the caking agents in drilling fluid 18 may be able to separate out of drilling fluid 18 and bond to serpentine passage 40. Should the flow velocity of drilling fluid 18 exceed approximately 4.54 m$^3$/h (20 gpm), particulate matter in drilling fluid 18 may begin to erode serpentine passage 40.

As shown in FIGS. 2A and 2B, front panel 42, middle panels 44, and back panel 46 can be stacked against one another inside interior 56 of container 38 to form serpentine passage 40. Middle panels 44 are disposed inside container 38 between front panel 42 and back panel 46. All of middle panels 44 can be identical to each other. It should be noted that while FIGS. 2A and 2B show that there are three middle panels 44, it is within the scope of this invention to combine middle panels 44 into a single middle panel 44. As discussed below with reference to FIGS. 3A-3C, middle panels 44 differ in geometry from front panel 42 and back panel 46, and can include at least twice as many openings as front panel 42 and back panel 46.

FIGS. 3A-3C will be discussed concurrently. FIG. 3A is a front elevation view of front panel 42 from the embodiment of drilling fluid monitoring system 34 shown in FIGS. 2A-2B. As shown in FIG. 3A, front panel 42 can include top end 62, bottom end 64, horizontal ribs $66_a$, $66_b$, vertical ribs 68, and openings $70_a$, $70_b$, $70_c$. Openings $70_a$ of front panel 42 can include a cross-sectional area with horizontal width $W1_a$ and vertical height $H1_a$. Openings $70_b$ of front panel 42 can include a cross-sectional area with horizontal width $W1_b$ and vertical height $H1_b$. Openings $70_c$ of front panel 42 can include a cross-sectional area with horizontal width $W1_c$ and vertical height $H1_c$.

FIG. 3B is a front elevation view of one of middle panels 44 from the embodiment of drilling fluid monitoring system 34 shown in FIGS. 2A-2B. As shown in FIG. 3B, each of middle panels 44 can include top end 72, bottom end 74, horizontal ribs 76, vertical ribs 78, and openings 80. Openings 80 of each middle panel 44 can include a cross-sectional area with horizontal width W2 and vertical height H2.

FIG. 3C is a front elevation view of back panel 46 from the embodiment of drilling fluid monitoring system 34 shown in FIGS. 2A-2B. As shown in FIG. 3C, back panel 46 can include top end 82, bottom end 84, horizontal ribs 86, vertical ribs 88, and openings 90. Openings 90 of back panel 46 can include a cross-sectional area with horizontal width W3 and vertical height H3.

Front panel 42 is formed by vertical ribs 68 which extend in the vertical direction from panel bottom 64 to panel top 62. Horizontal ribs 66a, 66b extend in the horizontal direction and intersect vertical ribs 68 to form openings $70_a$, $70_b$, $70_c$. Middle panels 44 (only one of which is shown in FIG. 3B) are formed by vertical ribs 78 which extend in the vertical direction from panel bottom 74 to panel top 72. Horizontal ribs 76 of middle panels 44 extend in the horizontal direction and intersect vertical ribs 78 to form openings 80. Back panel is formed by vertical ribs 88, which also extend in the vertical direction from panel bottom 84 to panel top 82. Horizontal ribs 86 of back panel 46 extend in the horizontal direction and intersect vertical ribs 88 of back panel 46 to form openings 90.

Openings $70_a$, $70_b$, $70_c$ of front panel 42, openings 80 of middle panels 44, and openings 90 of back panel 46 together form serpentine passage 40. Horizontal width W2 of openings 80 of middle panels 44 is uniform across all openings 80 of middle panels 44. Likewise, vertical height H2 of openings 80 of middle panels 44 is also uniform across all openings 80 of middle panels 44. Together, horizontal width W2 and vertical height H2 of openings 80 define a cross-sectional area for each opening 80 of middle panels 44. Because horizontal width W2 and vertical height H2 do not vary within openings 80, the cross-sectional area of each opening 80 of middle panels 44 is uniform with the rest of openings 80 of middle panels 44. In the embodiment of FIG. 3B, openings 80 can each have a uniform cross-sectional area of approximately 4.83 cm$^2$ (0.75 in$^2$) to approximately 7.29 cm$^2$ (1.13 in$^2$). Horizontal width W2 and vertical height H2 can be equal in length such that openings 80 of middle panels 44 are square.

Horizontal width W1$a$ and vertical height H1$_a$, both shown in FIG. 3A, define a cross-sectional area of openings 70$_a$. Horizontal width W1$_b$ and vertical height H1$_b$ define a cross-sectional area of openings 70$_b$, and horizontal width W1$_c$ and vertical height H1$_c$ define a cross-sectional area of openings 70$_c$. As shown in FIGS. 3A and 3B, horizontal width W1$_a$ of openings 70$_a$ of front panel 42 can be twice as wide as horizontal width W2 of openings 80 of middle panels 44. Vertical height H1$_a$ of openings 70$_a$ of front panel 42 can be equal in height with vertical height H2 of openings 80 of middle panels 44. By making horizontal width W1$_a$ of openings 70$_a$ of front panel 42 twice as wide as horizontal width W2 of openings 80 of middle panels 44, openings 70$_a$ allow serpentine passage 40 to turn within each level (as shown in FIGS. 2A and 2B).

Horizontal width W1$_b$ of openings 70$_b$ of front panel 42 can be equal in width with the horizontal width W2 of openings 80 of middle panels 44. Vertical height H1$_b$ of openings 70$_b$ can be twice as tall as vertical height H2 of openings 80 of middle panels 44. By making vertical height H1$_b$ of openings 70$_b$ twice as tall as vertical height H2 of openings 80 of middle panels 44, openings 70$_b$ allow serpentine passage 40 to descend levels within container 38 (as shown in FIG. 2A).

The dimensions of openings 70$_c$ of front panel 42 can be equal with the dimensions of openings 80 of middle panels 44. More specifically, horizontal width W1$_c$ of openings 70$_c$ can be equal in width with horizontal width W2 of openings 80, and vertical height H1$_c$ of openings 70$_c$ can be equal in height with vertical height H2 of openings 80. As shown in FIGS. 2A and 3A, front panel 42 includes two openings 70$_c$, one of which is disposed proximate container inlet 58 and the other is disposed proximate container outlet 60 when front panel 42 is assembled within container 38.

Horizontal width W3 can be uniform for all openings 90 of back panel 46. Vertical height H3 can also be uniform for all openings 90 of back panel 46. As shown in FIGS. 3B and 3C, horizontal width W3 of openings 90 can be twice as wide as horizontal width W2 of openings 80 on middle panels 44. Vertical height H3 of openings 90 of back panel 46 can be equal in height with vertical height H2 of openings 80 on middle panels 44. Similar to openings 70$_a$ of front panel 42, openings 90 of back panel 46 allow serpentine passage 40 to turn within each level (as shown in FIGS. 2A and 2B). Front panel 42, middle panels 44, and back panel 46 can be formed from any material with adequate stiffness and strength to resist deformation and erosion from the flow of drilling fluid 18, and that is substantially non-reactive to drilling fluid 18. For example, front panel 42, middle panels 44, and back panel 46 can be formed from stainless steel or aluminum. Container 38 can be formed from the same material as front panel 42, middle panels 44, and back panel 46.

Figure 4:
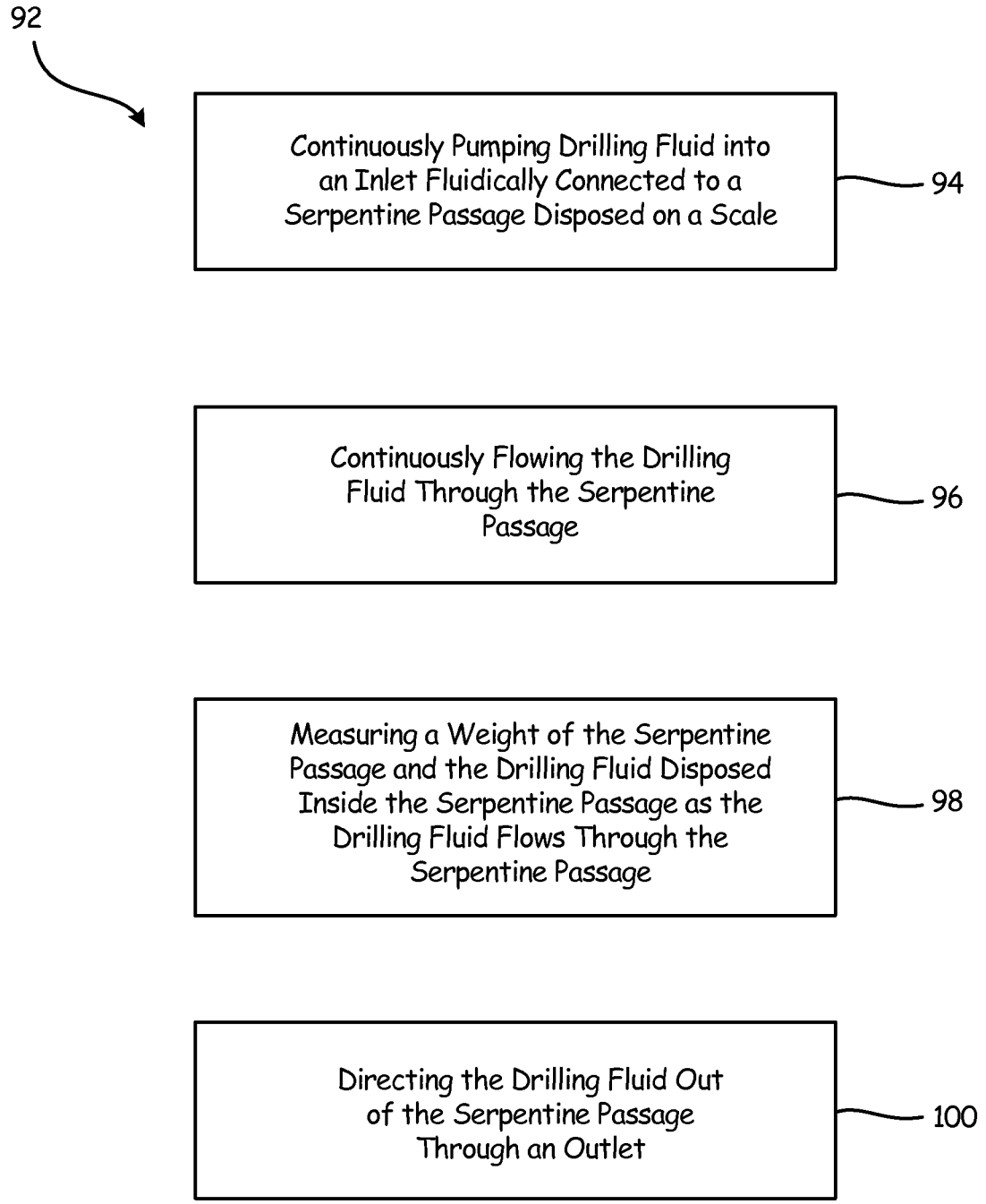
FIG. 4 is a block diagram of a method for measuring the weight of drilling fluid in a subterranean drilling operation.

FIG. 4 is a block diagram of method 92 employed by drilling fluid monitoring system 34 for measuring the weight of drilling fluid 18 during drilling of well 14 (shown in FIG. 1). As shown in FIG. 4, method 92 includes continuously pumping drilling fluid 18 into inlet 58 fluidically connected to serpentine passage 40 disposed on scale 36 (step 94). After entering inlet 58, drilling fluid 18 flows through serpentine passage 40 (step 96). As drilling fluid 18 flows through serpentine passage 40, scale 36 measures a weight of serpentine passage 40 and drilling fluid 18 disposed inside serpentine passage 40 (step 98). Drilling fluid 18 exits serpentine passage 40 via outlet 60 (step 100).

In view of the foregoing description, it will be recognized that the present disclosure provides numerous advantages and benefits. For example, the present disclosure provides drilling fluid monitoring system 34 with container 38, serpentine passage 40, and scale 36. Serpentine passage 40 is disposed inside container 38 and fluidically connected between container inlet 58 and container outlet 60. During operation, drilling fluid 18 flows continuously through serpentine passage 40 while scale 36 outputs a weight measurement, mass measurement, and/or density measurement of drilling fluid 18 at systematic intervals or continuously. Furthermore, the design of drilling fluid monitoring system 34 reduces the likelihood that caking agents will separate out of drilling fluid 18 inside drilling fluid monitoring system 34, thereby allowing drilling fluid monitoring system 34 to operate continuously for extended intervals of time without servicing. Furthermore, container inlet 58 is disposed proximate top side 52 of container 38, and container outlet 60 is disposed proximate bottom side 54 of container 38 such that drilling fluid 18 can drain out of serpentine passage 40 and container 38 without the need for additional flushing when drilling fluid monitoring system 34 is powered down or disconnected for servicing. It is beneficial that all of drilling fluid 18 drain out of drilling fluid monitoring system when not in operation so as to prevent caking agents in drilling fluid 18 from bonding to and building up within serpentine passage 40.

Any relative terms or terms of degree used herein, such as "substantially", "essentially", "generally", "approximately", and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, transitory vibrations and sway movements, temporary alignment or shape variations induced by operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A drilling fluid monitoring system comprising:
   a scale;
   a container disposed on the scale;
   a container inlet disposed proximate a top of the container;
   a container outlet disposed proximate a bottom of the container; and
   a serpentine passage disposed inside the container and fluidically connected to the container inlet and the container outlet.

2. The system of claim 1, wherein the container comprises:
   a plurality of panels stacked against one another inside the container, wherein each panel comprises:
      a plurality of vertically-oriented ribs; and
      a plurality of horizontally-oriented ribs intersecting the vertically-oriented ribs to form a plurality of openings; and
   wherein the plurality of openings of each of the plurality of panels together form the serpentine passage.

3. The system of claim 2, wherein the plurality of panels comprises:
   a first panel;
   a second panel; and
   a third panel,
   wherein the second panel is disposed inside the container between the first panel and the third panel and the second panel comprises at least twice as many openings as the first panel and the third panel.

4. The system of claim 3, wherein the plurality of openings of the second panel comprise a uniform cross-sectional area with a uniform horizontal width W2 and a uniform vertical height H2.

5. The system of claim 4, wherein at least one opening of the plurality of openings of the first panel comprises a cross-sectional area with a horizontal width $W1_a$ that is twice as wide as the horizontal width W2, and a vertical height $H1_a$ that is equal in height with the vertical height H2.

6. The system of claim 5, wherein at least one opening of the plurality of openings of the first panel comprises a cross-sectional area with a horizontal width $W1_b$ that is equal in width with the horizontal width W2, and a vertical height $H1_b$ that is twice as tall as the vertical height H2.

7. The system of claim 6, wherein at least one opening of the plurality of openings of the first panel comprises a cross-sectional area with a horizontal width $W1_c$ that is equal in width with the horizontal width W2, and a vertical height $H1_c$ that is equal in height with the vertical height H2.

8. The system of claim 3, wherein the plurality of openings of the third panel comprise a uniform cross-sectional area with a uniform horizontal width W3 that is twice as wide as the horizontal width W2, and a uniform vertical height H3 that is equal in height with the vertical height H2.

9. The system of claim 1, wherein the scale comprises:
   a wireless transmitter configured to transmit measurements made by the scale during operation of the drilling fluid monitoring system.

10. The system of claim 1, wherein the serpentine passage comprises a uniform cross-sectional flow area throughout a length of the serpentine passage.

11. The system of claim 10, wherein the cross-sectional flow area throughout the length of the serpentine passage is approximately 4.83 cm$^2$ (0.75 in$^2$) to approximately 7.29 cm$^2$ (1.13 in$^2$).

12. The system of claim 1, wherein the serpentine passage comprises a total flow volume of approximately 3.79 dm$^3$ (1.00 gal).

* * * * *